United States Patent [19]

Ancillotti et al.

[11] Patent Number: 5,194,656

[45] Date of Patent: Mar. 16, 1993

[54] CONTINUOUS INTEGRATED PROCESS FOR PRODUCING DIMETHYL CARBONATE AND METHYL TERT-BUTYL ETHER

[75] Inventors: Francesco Ancillotti, San Donato Milanese; Ermanno Pescarollo, Milan, both of Italy

[73] Assignee: Snamproggetti S.p.A., Milan, Italy

[21] Appl. No.: 867,329

[22] Filed: Apr. 13, 1992

[30] Foreign Application Priority Data

May 8, 1991 [IT] Italy ............................ 001258 A/91

[51] Int. Cl.$^5$ ............................................. C07C 69/96
[52] U.S. Cl. ..................................... 558/277; 568/697
[58] Field of Search ......................... 558/277; 568/697

[56] References Cited

FOREIGN PATENT DOCUMENTS 0038984 11/1981 European Pat. Off. ............ 558/277
0289232 11/1988 European Pat. Off. ............ 568/697

Primary Examiner—Mary C. Lee
Assistant Examiner—Joseph K. McKane
Attorney, Agent, or Firm—Oblon, Spivak, McClelland, Maier & Neustadt

[57] ABSTRACT

Dimethyl carbonate and methyl tert-butyl ether are prepared by a continuous integrated process comprising:

a) feeding methanol, carbon monoxide and oxygen into a reaction environment maintained under methanol oxidative carbonylation conditions, to form a liquid reaction mixture containing dimethyl carbonate and unaltered methanol;

b) at least partly eliminating the water from the reaction mixture of stage a);

c) feeding the dehydrated mixture of stage b) and isobutene, or a hydrocarbon fraction containing isobutene, into a reaction environment maintained under etherification conditions, to form a liquid reaction mixture containing dimethyl carbonate and methyl tert-butyl ether; and d) recovering the dimethyl carbonate and methyl tert-butyl ether from the reaction mixture of stage c).

9 Claims, 3 Drawing Sheets

CONTINUOUS INTEGRATED PROCESS FOR PRODUCING DIMETHYL CARBONATE AND METHYL TERT-BUTYL ETHER

This invention relates to a continuous integrated process for producing dimethyl carbonate and methyl tert-butyl ether. Methyl tert-butyl ether is an ether of significant commercial interest and is used as a gasoline additive. It is produced commercially by reaction isobutene with methanol over an acid catalyst, such as cationic ion exchange resin. For this known method reference should be made to the description of U.S. Pat. Nos. 3,979,461, 4,071,567 and 4,475,005.

Dimethyl carbonate is an extremely versatile product used as an organic solvent or as a reactant replacing phosgene in the synthesis of other alkyl or aryl carbonates used as synthetic lubricants, solvents, plasticizers and monomers for organic glasses, and in methylation and carbonylation reactions in the preparation of isocyanates, urethanes and polycarbonates.

The use of dimethyl carbonate or other organic carbonates or their mixtures with ethers, in particular methyl tert-butyl ether, has also been described as additive for gasolines or other heavier than gasoline fuels, to improve their antiknock characteristics. For this known technique reference should be made to the description of U.S. Pat. No. 2,331,386 and European patent applications 82,688 and 98,691.

Dimethyl carbonate can be prepared by oxidative carbonylation of methanol in the presence of copper catalysts, in accordance with the following reaction scheme:

$$2CH_3OH + CO + \tfrac{1}{2}O_2 \rightarrow (CH_3O)_2CO + H_2O$$

This reaction is conducted with an excess of methanol over the other reactants, and consequently on exit from the reaction system the product consists of a mixture of unconverted methanol with dimethyl carbonate and water as reaction products. The major drawback of this process is the difficulty of separating the reaction products because of the existence of azeotropic mixtures between the water and dimethyl carbonate and between the dimethyl carbonate and methanol. Specifically, to obtain pure dimethyl carbonate the methanol/dimethyl carbonate azeotrope has to be broken, for which certain methods have been proposed such as azeotropic distillation in the presence of a third component, for example chlorobenzene, or distillation under pressure, by which the azeotrope is nullified, or the use of special membranes.

According to the present invention, it has now been found possible to interact methanol with isobutene over an acid catalyst under typical etherification conditions, operating in the presence of dimethyl carbonate, without dimethyl carbonate hydrolysis problems arising. This makes it possible to produce methyl tert-butyl ether by reacting isobutene with the excess methanol contained in the methanol oxidative carbonylation products, without any previous separation.

One object of the present invention is therefore to prepare dimethyl carbonate and methyl tert-butyl ether by a continuous integrated process which results in a considerable reduction in investment and production costs. In this respect, it should be noted that dimethyl carbonate and methyl tert-butyl ether do not form azeotropic mixtures, hence overcoming the aforestated separation and purification problems of the known art.

It has also been found that the process of the present invention enables dimethyl carbonate and methyl tert-butyl ether to be produced in practically any desired ratio. A further object of the present invention is therefore to prepare mixtures of dimethyl carbonate and methyl tert-butyl ether which can be used directly as oxygenated gasoline additives. It should be noted that the use of dimethyl carbonate/methyl tert-butyl ether mixtures overcomes the problem of solidification which can occur if pure dimethyl carbonate is used, on account of its relatively high melting point of 4.6° C.

In accordance therewith, the present invention provides a continuous integrated process for producing dimethyl carbonate and methyl tert-butyl ether, comprising:

a) feeding methanol, carbon monoxide and oxygen into a reaction environment maintained under methanol oxidative carbonylation conditions, to form a liquid reaction mixture containing dimethyl carbonate and unaltered methanol;

b) at least partly eliminating the water from the reaction mixture of stage a);

c) feeding the dehydrated mixture of stage b) and isobutene, or a hydrocarbon fraction containing isobutene, into a reaction environment maintained under etherification conditions, to form a liquid reaction mixture containing dimethyl carbonate and methyl tert-butyl ether; and d) recovering the dimethyl carbonate and methyl tert-butyl ether from the reaction mixture of stage c).

Stage a)

In stage a) of the process, dimethyl carbonate is prepared in accordance with the following reaction scheme:

$$2CH_3OH + CO + \tfrac{1}{2}O_2 \rightarrow (CH_3O)_2CO + H_2O$$

The reaction is catalyzed by a methanol oxidative carbonylation catalyst, in particular a copper catalyst, generally in the form of cuprous chloride.

The practical procedure comprises feeding a liquid methanol stream and a gaseous carbon monoxide and oxygen stream into a liquid reaction mixture of constant or essentially constant composition in which the catalyst is suspended.

Conveniently, the liquid mixture composition is kept constant within the following ranges:

methanol 35-70% by weight, water 2-8% by weight, the remainder consisting essentially of dimethyl carbonate and the inevitable impurities. The liquid reaction mixture also contains the copper catalyst in a quantity of 5-30 parts by weight, evaluated as cuprous chloride, per 100 parts by weight of the mixture.

The carbon monoxide and oxygen can be fed as separate streams or mixed, and can be in pure form or diluted with inert gases such as nitrogen, hydrogen and methane. Conveniently, an excess of methanol over the stoichiometric is used, under conditions of substantially complete conversion of the carbon monoxide. The reaction temperature can generally vary from 70° to 150° C., and is preferably within the range of 120°-140° C. The operating pressure can vary within wide limits and is such as to maintain the reaction mixture in the liquid phase at the operating temperature. The preferred pressure is within the range of 15-40 kg/cm².

Stage a) of the process can be performed in one or more methanol oxidative carbonylation reactors, from which a spent gaseous stream and a liquid stream containing dimethyl carbonate, water and unconverted methanol of the aforestated composition are discharged, this latter being fed to the dehydration stage b), after separating the catalyst.

Stage b)

In stage b) of the process, the liquid stream from stage a) is subjected to at least partial dehydration.

The dehydration can be achieved by distilling the liquid stream in a distillation column, in which the water is separated as the bottom stream. It is also possible to add fresh and/or recycled methanol to the liquid stream before distillation, in order to separate the water as bottom stream from a dimethyl carbonate/methanol mixture having a composition equal or close to azeotropic. The dehydrated stream is fed to stage c) of the process after mixing with isobutene or with a $C_4$ hydrocarbon fraction containing isobutene.

In a further embodiment, the liquid stream from stage a) is mixed with isobutene or with a $C_4$ hydrocarbon fraction containing isobutene (such as the $C_4$ fraction from the pyrolysis of naphtha, before or preferably after butadiene separation) and possibly with water, to induce separation of a light liquid phase rich in $C_4$ hydrocarbons, low in water and containing a good part of the dimethyl carbonate, from a heavy liquid phase rich in water and methanol and containing the remaining part of the dimethyl carbonate. In this case the water is separated from the heavy phase as bottom product in a distillation column, the overhead product (containing methanol and dimethyl carbonate) being combined with the light liquid phase and then fed to the etherification stage c).

In all cases, the operations involved in stage b) are conducted in such a manner as to feed to stage c) a stream which is free of water or contains less than about 1% by weight of water, and in which the methanol-/isobutene molar ratio is conveniently between 0.8/1 and 1.2/1.

Stage c)

In stage c) of the process, methyl tert-butyl ether is prepared in accordance with the following reaction scheme:

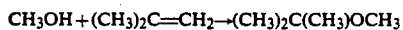

The reaction is catalyzed by an acid catalyst, especially a macroporous cationic ion exchange resin. Examples of such resins are macroreticular sulphonated styrene/divinylbenzene resins having for example an exchange capacity of 4.8 meq/g (on a dry basis). Examples of suitable commercial resins are Amberlyst®15, Dowex®M15 and Lewatit®SPC 118.

In practice, the liquid stream from stage b) is fed to the cationic ion exchange resin in the form of a fixed bed, the etherification reaction being conducted in the liquid phase at a temperature of 40°–100° C. (preferably of the order of 55° C.), under a pressure of 10–40 kg/cm² (preferably of the order of 20 kg/cm²) and with a space velocity of the order of 7 hour$^{-1}$. Under these conditions the methanol reacts selectively with the isobutene to form methyl tert-butyl ether with the absence or substantial absence of hydrolysis phenomena or of degradation of the dimethyl carbonate present in the reaction environment.

The liquid stream discharged from stage c) contains dimethyl carbonate and methyl tert-butyl ether in a weight ratio generally of between 5:95 and 95:5, and preferably between 15:85 and 20:80, together with smaller quantities of unaltered methanol and isobutene and possibly inert $C_4$ hydrocarbons.

Stage d)

The liquid stream from stage c) is treated to separate dimethyl carbonate and methyl tert-butyl ether. A first distillation column can be used to separate the dimethyl carbonate and methyl tert-butyl ether mixture at the bottom and the lighter components consisting of $C_4$ hydrocarbons and methanol at the top. The dimethyl carbonate/methyl tert-butyl ether mixture can be separated into its two constituents without difficulty. However, in a preferred embodiment the mixture is used directly as a gasoline additive, as described in greater detail hereinafter. The light stream can be washed with water to separate the $C_4$ hydrocarbons from an aqueous methanol stream. This latter is finally conveniently distilled to separate the methanol, which is then recycled.

As stated heretofore, the process of the present invention enables mixtures of dimethyl carbonate and methyl tert-butyl ether to be directly obtained for direct use as gasoline additives. The reasons for such a use are as follows. With the elimination of lead alkyls from gasolines, the high-octane oxygenated compounds such as low molecular weight alcohols and alkyl tert-alkyl ethers have bridged the gap between the octane level economically attainable in the refinery and the octane requirement of the motor vehicle, so enabling unleaded gasolines to attain a high market share without causing excessive vehicle disturbance. Current developments in the introduction of reformulated gasolines to the U.S. market and the requirements of the Clean Air Act (CAA) in terms of the maximum ozone and carbon monoxide content of the air mean that oxygenated compounds will be assigned the further function of ensuring a minimum oxygen level within gasolines. The oxygen content of reformulated gasolines is currently around 1.5% by weight. By the end of 1992, gasolines within those areas which do not conform to the carbon monoxide standard (41 areas) will have to contain a minimum of 2.7% of oxygen for at least four winter months, whereas from 1995 in those areas which do not conform to the ozone standard (9 areas) gasolines with a minimum of 2% of oxygen will have to be used. Even higher oxygen values can be assumed in subsequent periods. These standards currently relate to the U.S. market, however it is not improbable that the European Community bodies will in the future adopt minimum oxygen content measures.

The double function of octanizer and oxygenizer attributed to the oxygenated compounds within gasolines results in a diversification of the various alcohols and ethers, not only in terms of their octane behaviour but also in terms of their oxygen content within the molecule, as is apparent from the following Table 1.

TABLE 1

| Characteristics of oxygenated products | | | | | | |
|---|---|---|---|---|---|---|
| | methanol | ethanol | MTBE | ETBE | TAME | DCM |
| Density | 0.7960 | 0.7936 | 0.7456 | 0.7456 | 0.7750 | 1.07 |
| RON* | 125 | 123 | 116 | 118 | 111 | 110 |
| MON* | 91 | 96 | 98 | 105 | 94 | 97 |
| (RON + MON)/2* | 108 | 109 | 107 | 111 | 102 | 104 |
| Oxygen wt % | 50 | 34.7 | 18.1 | 15.7 | 15.7 | 53.3 |
| B.P. (°C.) | 65 | 78 | 55 | 73 | 86 | 90.5 |
| Blending** volatility, psi | 58–62 | 18–22 | 8–10 | 3–5 | 1–2 | <1** |

MTBE = methyl tert-butyl ether
ETBE = ethyl tert-butyl ether
TAME = methyl tert-amyl ether
DMC = dimethyl carbonate
RON = Research octane number
MON = Motor octane number
*Base gasoline values (RON + MON)/2 = 89.3 and RON − MON = 10;
**Values from G. H. Unzelman, O.G.J., 9 April 1990 p 43;
***Estimated value.

As can be seen from Table 1, while the octane values are not excessively diversified, at least at the (RON+MON)/2 level, the oxygen content falls considerably in going from the alcohols to the ethers. The blending volatility decreases in the same direction. The high volatility of the alcohols is related to their capacity to form minimum azeotropes with the hydrocarbons, a characteristic which ethers do not possess/ As can be also seen from Table 1, dimethyl carbonate has a higher oxygen content than methanol but a considerably reduced volatility. If the objective were merely to attain a minimum oxygen value, it is apparent that this could be achieved with the minimum volume of oxygenated product by using components of high oxygen concentration such as alcohols and dimethyl carbonate. It seems however that alcohols are not components of high interest for reformulated gasoline because of their tendency to come out of mixture, so limiting pipeline transfer of the gasolines which contain them, and because of their high blending volatility which is difficult to reconcile with the need for limiting evaporative emissions. Dimethyl carbonate could therefore represent the choice component for the oxygenating function alone.

However, there is a double objective to be achieved, i.e. to optimize the addition of oxygenating products such as to simultaneously satisfy both the octane value and the oxygen level. This objective is difficult to achieve using a single product or more than one product of the same class, as is apparent from the data of Table 2 below.

TABLE 2

| % of oxygenating components required to obtain determined oxygen levels (w = weight; v = volume) | | | | | | |
|---|---|---|---|---|---|---|
| Oxygen level | 2% | | 2.7% | | 3.5% | |
| % oxygenated comps | w | v | w | v | w | v |
| MTBE | 11.05 | 10.91 | 14.90 | 14.65 | 19.33 | 19.10 |
| ETBE | 12.74 | 12.58 | 17.20 | 17.00 | 22.29 | 22.04 |
| TAME | 12.74 | 12.16 | 17.20 | 16.46 | 22.29 | 21.38 |
| DMC | 3.74 | 2.59 | 5.06 | 5.32 | 6.55 | 4.59 |
| MIXT1 | 8.60 | 8.14 | 11.62 | 11.02 | 15.05 | 14.28 |
| MIXT2 | 7.95 | 7.41 | 10.74 | 10.01 | 13.92 | 12.97 |

NB: MIXT1 is a mixture of 85.6 wt % MTBE and 14.4 wt % DMC; MIXT2 is a mixture of 80.0 wt % MTBE and 20.0 wt % DMC.

The reference gasoline has a density of 0.7350 g/ml at 15° C. Table 2 shows the quantity of oxygenated compounds which must be added to achieve predetermined oxygen levels.

Table 3 below shows the octane increase in terms of (RON+MON)/2 achieved with the various compounds according to the oxygen percentage introduced.

TABLE 3

| | Increase in (RON + MON)/2 for the indicated oxygen percentages | | |
|---|---|---|---|
| % oxygen | 2 | 2.7 | 3.5 |
| MTBE | 1.93 | 2.64 | 3.38 |
| ETBE | 2.72 | 3.67 | 4.76 |
| TAME | 1.54 | 2.09 | 2.70 |
| DMC | 0.38 | 0.51 | 0.59 |
| MIXT1 | 1.40 | 1.89 | 2.45 |
| MIXT2 | 1.27 | 1.72 | 2.22 |

A (RON+MON)/2 value of 106.5 has been assumed for MIXT1 and MIXT2.

The ethers have a relatively low oxygen content in the molecule, so that large volumes have to be used to introduce large oxygen percentages into the fuel, and this at least in the medium term can result in an insufficient availability and even a probable octane excess only partly controllable on the basis of the octane level of the gasoline hydrocarbon base. In contrast, because of its high oxygen percentage in the molecule, dimethyl carbonate can achieve the specific minimum oxygen level in the fuel with a small volume, but with a correspondingly low octane effect. Instead, the mixtures MIXT1 and MIXT2 achieve the double optimization relative to the quantity added and the octane effect produced. To produce these or similar mixtures, dimethyl carbonate and methyl tert-butyl ether can evidently be mixed together in suitable proportions. However, with the process of the present invention these mixtures can be obtained directly in a simple and economical manner.

FIG. 1 of the drawing shows a simplified process scheme for preparing dimethyl carbonate by the known art.

Figure 1:
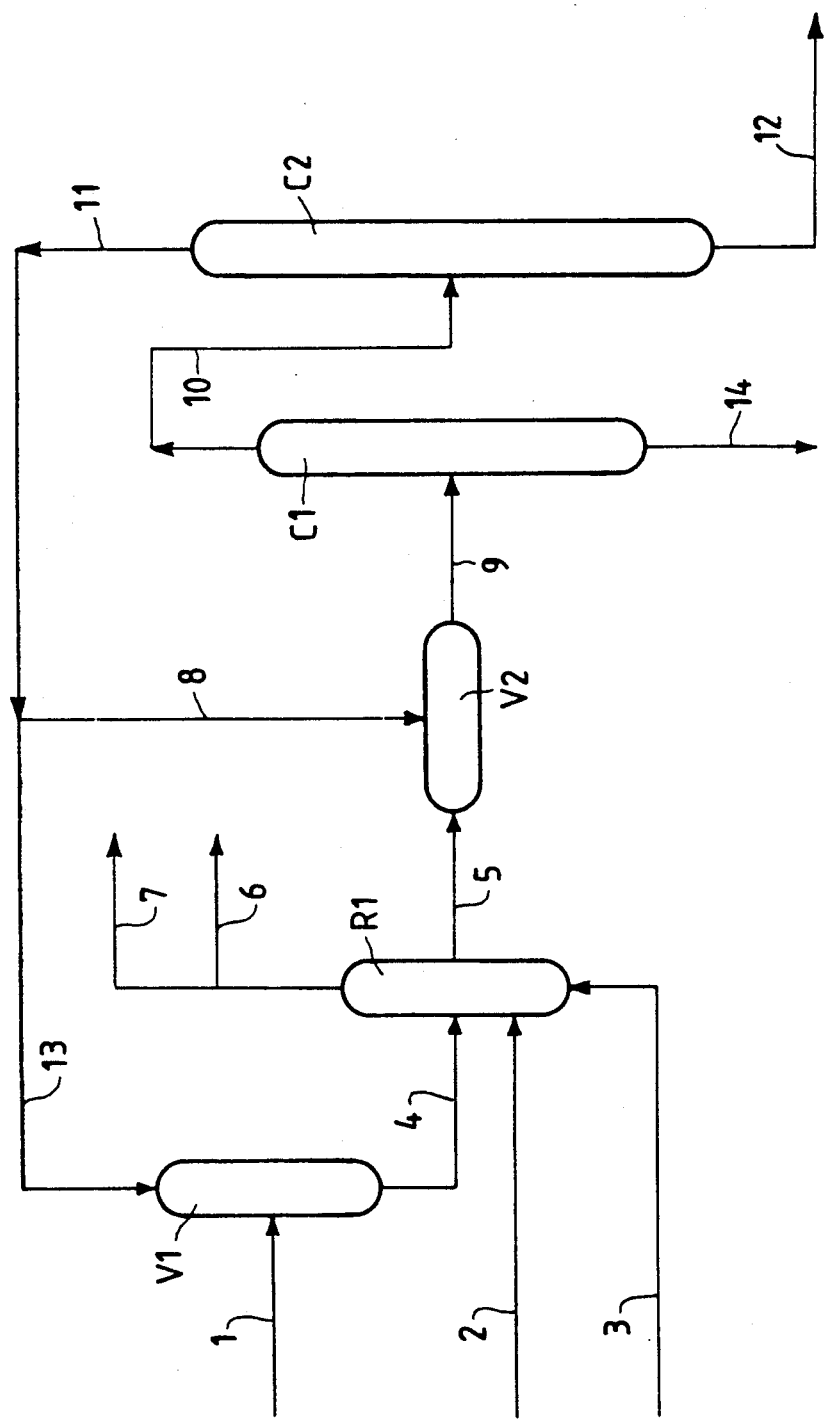

With reference to FIG. 1, a fresh methanol stream 1 and a recycle methanol stream 13 are fed to the vessel V1, the two combined streams 4 then being fed to the dimethyl carbonate synthesis reactor R1. An oxygen stream 2 and a carbon monoxide stream 3 are also fed to the reactor R1. The process is carried out in the reactor R1 in the liquid phase in the presence of a copper catalyst under methanol oxidative carbonylation conditions, to produce two spent gas streams 6 and 7 and a liquid stream 5 containing dimethyl carbonate, water and the excess methanol. According to the known art this liquid reaction mixture is fed to the vessel V2 together with a recycle stream 8, the resultant stream 9 undergoing distillation in the column C1 to separate the water as bottom stream 14. The overhead stream 10, having generally the composition of the azeotrope (70% methanol, 30% dimethyl carbonate) is fractionated in the column C2 under azeotrope breakdown conditions, to obtain a dimethyl carbonate stream 12, which is recovered, and a methanol stream (11), which is recycled.

The following experimental examples are provided to better illustrate the present invention.

EXAMPLE 1

Figure 2:
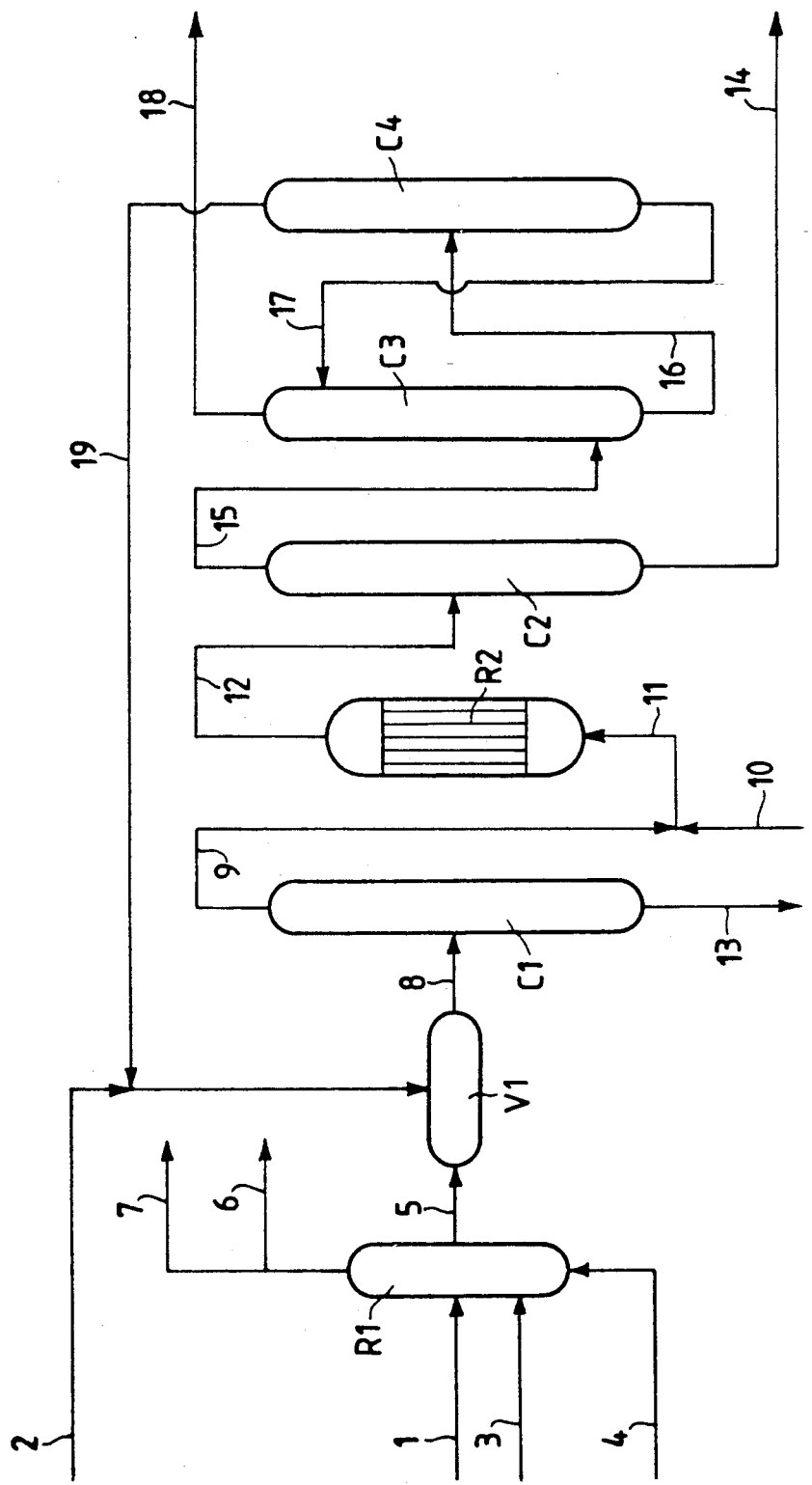
FIG. 2 shows a simplified scheme of the continuous integrated process for producing dimethyl carbonate and methyl tert-butyl ether in accordance with one embodiment of the present invention.

With reference to FIG. 2, a liquid methanol stream 1 (2392 kg/hour) containing make-up catalyst in suspension, an oxygen stream 3 (215 kg/hour) and a stream 4 of carbon monoxide and hydrogen (441 kg/hour and 16 kg/hour respectively) are fed to the dimethyl carbonate synthesis reactor R1. The process is carried out in the reactor R1 in the liquid phase at a temperature of 120° C. and a pressure of 25 kg/cm$^2$, in the presence of a copper catalyst in the form of cuprous chloride. Under these conditions, the reactor R1 discharges 2934 kg/hour of a liquid stream 5 containing dimethyl carbonate (1119 kg/hour), unaltered methanol (1590 kg/hour) and water (225 kg/hour), and 130 kg/hour of gaseous streams, of which the stream 7 is fed to fuel (56 kg/hour) and the stream 6 is vented to the flare (74 kg/hour).

The stream 5 is mixed in the vessel V1 with a fresh and recycle methanol stream 2 (1040 kg/hour), the resultant stream 8 being fed to a fractionation column C1, from the bottom of which water is discharged as the stream 13, and from the top of which a stream 9 of 3748 kg/hour is withdrawn consisting essentially of methanol (2629 kg/hour) and dimethyl carbonate (1119 kg/hour).

The stream 9 is mixed with a stream 10 consisting of 9218 kg/hour of a C$_4$ fraction containing 50 wt % of isobutene, the resultant stream 11 being fed to the reactor R2 containing the commerical ion exchange resin Amberlyst ®CSP in the form of a fixed bed. Methyl tert-butyl ether forms in the reactor R2 operating at a temperature of about 60° C. and with a space velocity of about 7 hour$^{-1}$, to discharge 22,966 kg/hour of a liquid stream 12 containing inert butenes (4609 kg/hour), unaltered isobutene (366 kg/hour), methanol (206 kg.hour), dimethyl carbonate (1119 kg/hour) and methyl tert-butyl ether (6666 kg/hour).

The stream 12 is fed to the distillation column C2 to obtain an overhead gaseous stream 15 containing inert butenes, isobutene and methanol, and a bottom liquid stream 14 containing dimethyl carbonate and methyl tert-butyl ether.

The stream 15 is washed in the column C3 with a recycle water stream 17 to separate the C$_4$ hydrocarbons, as overhead stream, from a liquid bottom stream 16 of aqueous methanol. The stream 16 is fractionated in the column C4 to separate a methanol stream 19, which is recycled.

EXAMPLE 2

Figure 3:
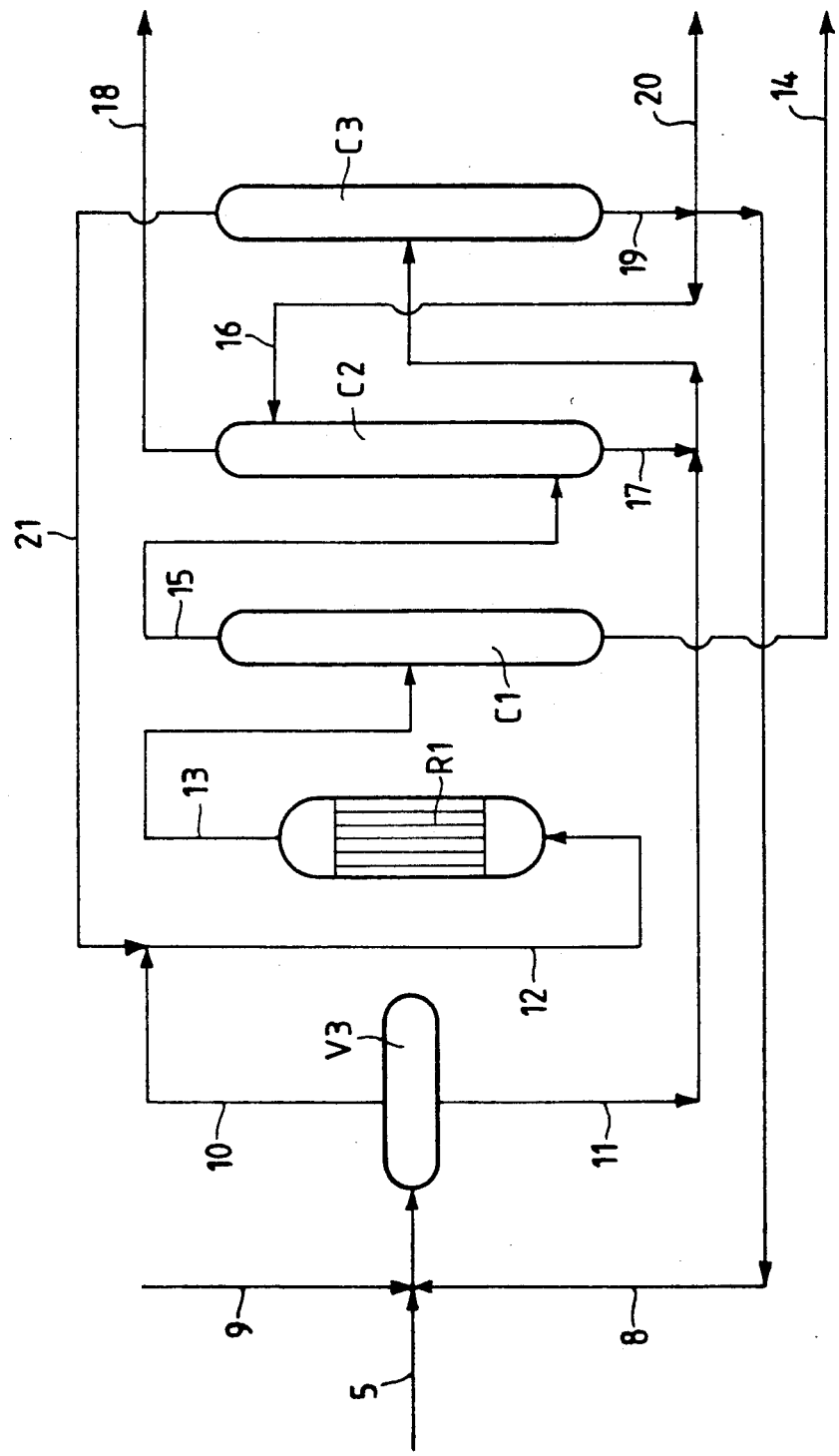
FIG. 3 shows a simplified scheme of the continuous integrated process for producing dimethyl carbonate and methyl tert-butyl ether in accordance with a further embodiment of the present invention.

In this example the dimethyl carbonate production part is identical to that of Example 1 as far as the production of a liquid stream 5 of 2934 kg/hour containing dimethyl carbonate (1119 kg/hour), unaltered methanol (1590 kg/hour) and water (225 kg/hour). With reference to the scheme shown in FIG. 3, said stream 5 is mixed with a recycle water stream 8 (686 kg/hour) and with a C$_4$ hydrocarbon stream 9 containing 50 wt % of isobutene (5922 kg/hour). Mixing is carried out in a static mixer which enables phase equilibrium to be achieved, the resultant turbid liquid being fed to the decanter V3, where two phases form. The upper phase is withdrawn at a rate of 6733 kg/hour as the stream 10 and consists of methanol (87 kg/hour), dimethyl carbonate (745 kg/hour), water (8 kg/hour) and C$_4$ hydrocarbons (5893 kg/hour). The lower phase is withdrawn at a rate of 2809 kg/hour as the stream 11 and consists of methanol (1503 kg/hour), dimethyl carbonate (374 kg/hour), water (903 kg/hour) and C$_4$ hydrocarbons (29 kg/hour). The stream 11 is fed to the distillation column C3, while the stream 10 is mixed with a 2008 kg/hour recycle stream 21 from the top of the column C3 and containing methanol (1604 kg/hour), dimethyl carbonate (374 kg/hour) and C$_4$ hydrocarbons (29 kg/hour). The resultant stream from the mixing is fed as the stream 12 to the reactor R2 for methyl tert-butyl ether synthesis operating under conditions similar to those of Example 1. The reaction products are withdrawn from R2 as a stream 13 containing unconverted methanol (102 kg/hour), dimethyl carbonate (1119 kg/hour), water (2.5 kg/hour), inert hydrocarbons (2961 kg/hour), unconverted isobutene (160 kg/hour), methyl tert-butyl ether (4373 kg/hour) and tert-butyl alcohol (23.5 kg/hour). The stream 13 is fed to the fractionation column C1, from the bottom of which a mixture of dimethyl carbonate (1119 kg/hour), methyl tert-butyl ether (4373 kg/hour) and tert-butyl alcohol (23.5 kg/hour) is recovered. The composition of this mixture is similar to that of the mixture MIXT2 described in the aforegoing description. A stream 15 is withdrawn from the top of the column C3 containing methanol (102 kg/hour) and water (2.5 kg/hour) in addition to C$_4$ hydrocarbons. The stream 15 is fed to the column C2 for extraction with water, this latter being fed as the recycle stream 16 at a rate of 300 kg/hour. The refined product consisting of C$_4$ hydrocarbons is recovered from the top of the column C2 and is fed to storage as the stream 18. An extract is also obtained from the column C2 consisting of methanol (102 kg/hour) and water (302.5 kg/hour), this being combined with the stream 11 and the mixture fed to the recovery column C3. In the column C3 a bottom stream 19 of 1205 kg/hour of water is obtained, part of which is recycled as streams 8 and 16, and the remainder is discharged through 20.

The stream 21 is obtained from the top of the column C3 and is recycled as already described.

EXAMPLE 3

The procedure is similar to Example 2 but with the difference that 5539 kg/hour of a C$_4$ fraction containing 50 wt % of isobutene are added to the stream 5. The resultant mixture is allowed to separate in V1, with the formation of an upper liquid phase of 6389 kg/hour containing 4.9 wt % of methanol, 11.5 wt % of dimethyl carbonate, 0.3 wt % of water and 83.3 wt % of $C_4$ fraction, and a lower liquid phase of 2084 kg/hour containing 61.2 wt % of methanol, 18.4 wt % of dimethyl carbonate, 10.0 wt % of water and 10.4 wt % of $C_4$ fraction.

The two liquid phases are treated as described in Example 2, producing similar results.

EXAMPLE 4

The procedure is similar to Example 2 but with the difference that a 7390 kg/hour stream consisting of 5539 kg/hour of a $C_4$ fraction containing 50 wt % of isobutene and 1851 kg/hour of water are added to the stream 5. The resultant mixture is allowed to separate in V1, with the formation of an upper liquid phase of 6409 kg/hour containing 8987 ppm of methanol, 12.6 wt % of dimethyl carbonate, 1420 ppm of water and 86.3 wt % of $C_4$ fraction, and a lower liquid phase of 3915 kg/hour containing 39.1 wt % of methanol, 7.9 wt % of dimethyl carbonate, 52.8 wt % of water and 1377 ppm of $C_4$ fraction.

The two liquid phases are treated as described in Example 2, producing similar results.

EXAMPLE 5

The procedure is similar to Example 2 but with the difference that a 9980 kg/hour stream consisting of 5539 kg/hour of a $C_4$ fraction containing 50 wt % of isobutene and 4441 kg/hour of water are added to the stream 5. The resultant mixture is allowed to separate in V1, with the formation of an upper liuqid phase of 6357 kg/hour containing 4216 ppm of methanol, 12.3 wt % dimethyl carbonate, 1318 ppm of water and 87.1 wt % of $C_4$ fraction, and a lower liquid phase of 6557 kg/hour containing 23.8 wt % of methanol, 5.1 wt % of dimethyl carbonate, 71 wt % of water and 200 ppm of $C_4$ fraction.

The two liquid phases are treated as described in Example 2, producing similar results.

We claim:

1. A continuous integrated process for producing dimethyl carbonate and methyl tert-butyl ether, comprising the steps of:
   a) feeding a liquid methanol stream and a gaseous carbon monoxide and oxygen stream into a liquid reaction mixture of constant or essentially constant composition, in which a copper catalyst is suspended and which contains 35-70 wt. % of methanol and 2-8 wt. % of water, the remainder consisting essentially of dimethyl carbonate and inevitable impurities, the operating temperature being 70°-150° C. and the operating pressure being such as to maintain the reaction mixture in the liquid phase, to form a liquid reaction mixture containing dimethyl carbonate and unaltered methanol;
   b) at least partly eliminating the water from the reaction mixture of stage a);
   c) feeding the dehydrated mixture of stage b) and isobutene, or a hydrocarbon fraction containing isobutene, into a cationic ion exchange resin arranged in the form of a fixed bed, the etherification reaction being conducted in the liquid phase at a temperature of 40°-100° C., under a pressure of 10–40 kg/cm$^2$ and with a space velocity of about 7 hr$^{-1}$, to form a liquid reaction mixture containing dimethyl carbonate and methyl tert-butyl ether; and
   d) recovering the dimethyl carbonate and methyl tert-butyl ether from the reaction mixture of stage c).

2. A process as claimed in claim 1, characterised in that in stage b) the liquid stream from stage a) is distilled in a distillation column, in which the water separates as bottom stream.

3. A process as claimed in claim 1, characterised in that in stage b) the liquid stream from stage a) is mixed with isobutene or with a $C_4$ hydrocarbon stream containing isobutene and possibly also with water, to separate a light liquid phase rich in $C_4$ hydrocarbons, low in water and containing a good part of the dimethyl carbonate, from a heavy liquid phase rich in water and methanol and containing the remainder of the dimethyl carbonate, this latter being free of water and being combined with the light fraction, the resultant mixture being fed to the etherification stage c).

4. A process as claimed in claim 1, characterised in that in stage c) a macroporous cationic ion exchange resin of sulphonated styrene/divinylbenzene type is used having an ion exchange capacity of about 4.8 meq/g (on a dry basis).

5. A process as claimed in claim 1, characterised in that in stage d) the liquid stream from stage c) is fractionated in a first distillation column to separate the dimethyl carbonate and methyl tert-butyl ether mixture at the bottom and the lighter constituents at the top.

6. A process as claimed in claim 1, wherein the operating temperature of stage a) is 120°-140° C.

7. A process as claimed in claim 1, wherein the operating pressure of stage a) is 15-40 kg/cm$^2$.

8. A process as claimed in claim 1, wherein the temperature of stage c) is about 55° C.

9. A process as claimed in claim 1, wherein the pressure in stage c) is about 20 kg/cm$^2$.

* * * * *